US007945022B2

(12) United States Patent
Nelms et al.

(10) Patent No.: US 7,945,022 B2
(45) Date of Patent: May 17, 2011

(54) RADIATION THERAPY PLAN DOSE PERTURBATION SYSTEM AND METHOD

(75) Inventors: Benjamin E. Nelms, Merrimac, WI (US); William E. Simon, Melbourne, FL (US)

(73) Assignee: Sun Nuclear Corp., Melbourne, FL (US)

( * ) Notice: Subject to any disclaimer, the term of this patent is extended or adjusted under 35 U.S.C. 154(b) by 35 days.

(21) Appl. No.: 12/402,785

(22) Filed: Mar. 12, 2009

(65) Prior Publication Data
US 2009/0252292 A1    Oct. 8, 2009

Related U.S. Application Data

(60) Provisional application No. 61/035,834, filed on Mar. 12, 2008.

(51) Int. Cl.
*A61N 5/10* (2006.01)
(52) U.S. Cl. ........................................... 378/65
(58) Field of Classification Search .................. 378/65
See application file for complete search history.

(56) References Cited

U.S. PATENT DOCUMENTS

| | | | |
|---|---|---|---|
| 5,640,436 | A | 6/1997 | Kawai et al. |
| 6,594,336 | B2 | 7/2003 | Nishizawa et al. |
| 6,853,702 | B2 | 2/2005 | Renner |
| 2003/0138077 | A1 | 7/2003 | Lee |
| 2004/0228435 | A1 | 11/2004 | Rusell |
| 2005/0077459 | A1 | 4/2005 | Engler et al. |
| 2006/0203964 | A1 | 9/2006 | Nyholm et al. |

OTHER PUBLICATIONS

Benedick Fraass; "Quality Assurance for Clinical Radiotherapy Treatment Planning,"Med Phys., 25 (10), Oct. 1998; pp. 1773-1829.
G.J. Kutcher; "Comprehensive AQ for Radiation Oncology Report"; AAPM Radiation Therapy Committee Task Group 40; Med. Phys., 21; Apr. 1994; pp. 581-618.
MapCheck and EPIDose; www.sunnuclear.com; manufactured by Sun Nuclear Corp.; Melbourne, FL; 2010.
MapCALC; www.sunnuclear.com; manufactured by Sun Nuclear Corp., Melbourne, FL; 2009.
Joseph O. Deasy; "A Computational Environment for Radiotherapy Research,", Med. Phys. 30, (5), May 2003; pp. 979-985.
Robert M. Eisberg; "Fundamentals of Modern Physics,"; Chapter 9—Perturbation Theory; John Wiley & Sons; 1967; pp. 268-272.
Cyberknife; Cyberknife System; "The Standard of Radiosurgery" by Accuray, Sunnyvale, CA; 2009; pp. 1-6.
"Hi-Art,"; www.tomotherapy.com; TomoTherapy, Madison, WI; 2007; pp. 1-8.
"Rapid Arc"; Varian Medical Systems, Inc., Palo Alto, CA; www.varian.com; 2007; pp. 1-8.

(Continued)

*Primary Examiner* — Chih-Cheng G Kao
(74) *Attorney, Agent, or Firm* — Allen, Dyer, Doppelt, Milbrath & Gilchrist, P.A.

(57) ABSTRACT

A method of determining a patient dose during or prior to therapy from an external radiation beam includes determining a dose distribution from a patient plan as delivered in a QA phantom at each appropriate beam angle and comparing the dose distribution determined from measurements or calculations to a corresponding treatment planning system (TPS) dose modeled distribution in the QA phantom and providing a correction distribution when applied to the TPS dose modeled distribution results in the dose distribution determined. The correction distribution may optionally be interpolated to non-measured points for each beam angle and geometrically projected toward the source of radiation through a volume that equals a dose volume of the TPS for a patient beam for each beam angle. The correction distribution is applied to the TPS patient dose volume for each beam angle for providing a corrected dose distribution in the patient.

39 Claims, 5 Drawing Sheets

OTHER PUBLICATIONS

"VMAT"; Elekta, Ltd., Crawley UK; Document No. 4513 3710770; Oct. 8, 2008.

D.W.O. Rogers; "Montey Carlo Techniques in Radiotherapy,"; Physics in Canada, Medical Physics Special Issue, v. 58 #2; 2002; pp. 63-70.

T.R. McNutt, T.R. Mackie, P.J. Reckwerdt, B.R. Paliwal; "Modeling Dose Distributions from Portal Dose Images Using the Convolution/Superposition Method,"; Med. Phys. 23(8); Aug. 1996; pp. 1381-1392.

T.R. McNutt, T.R. Mackie, P.J. Reckwerdt, B.R. Paliwal; "Analysis and Convergence of the Iterative Convolution/Superposition Dose Reconstruction Technique,"; Med. Phys. 24(9) Sep. 1997; pp. 1465-1476.

Mathilda Van Zijtveld, Maarten L.P. Dirkxa, Hans C.J. De Boera, and Ben J.M. Heijmen; "3D Dose Reconstruction for Clinical Evaluation of IMRT Pretreatment Verification with an EPID," Radiotherapy and Oncology, 82(2); Feb. 2007; pp. 201-201.

RADIATION THERAPY PLAN DOSE PERTURBATION SYSTEM AND METHOD

CROSS REFERENCE TO RELATED APPLICATION

This application incorporates the disclosures by reference and claims priority to Provisional application Ser. No. 61/035,834 filed Mar. 12, 2008 for "Three Dimensional Dosimetry Using Solid Array Geometry," and to U.S. utility patent application Ser. No. 12/401,949 filed Mar. 11, 2009 for "Three Dimensional Dosimetry Using Solid Array Geometry," all commonly owned.

FIELD OF INVENTION

The invention generally relates to radiation therapy dose delivery quality assessment (QA), and in particular to systems and methods for measuring and localizing, spatially and/or temporally, the dose in a phantom for supporting QA of the dose in a patient during radiation therapy beam delivery.

BACKGROUND

There is a need for an accurate assessment of the dose delivery to the oncology patient during external beam radiation therapy. A direct assessment is virtually impossible due to the location of the radiation target inside the human body that is comprised of complex shapes and material compositions that have an affect on the radiation delivery, to say nothing of the complexity of the delivery controls that have evolved over the past decade. Great strides have been made in the planning and calculations of dose transport and deposition in the heterogeneous human anatomy; there are several independent types of calculation models that are used by these treatment planning systems (TPS), all with particular strengths and weaknesses. The clinician must ultimately rely on the TPS dose assessment tools to evaluate the treatment plan's potential for success and risk. One of these tools is the dose volume histogram (DVH), which is a statistical formulation of 3D dose coverage (of targets) and sparing (of critical structures) to allow a metric, or ranking, by which to assess, compare, and approve treatment plans.

There are a number of approaches to validate the planned dose delivery. The elemental approach is to validate all elements of the chain that lead from plan to delivery, starting with rigorous verification of the plan dose modeling (as described in Benedick Fraass, et al, American Association of Physicists in Medicine Radiation Therapy Committee Tasg Group 53: Quality assurance for clinical radiotherapy treatment planning", Med. Phys., 25, (10), October 1998, pp 1773), eliminating all weakness of the TPS from the actual plan, performing rigorous quality assurance (QA) testing of the delivery system 2 (as addressed in G. J. Kutcher, et al, "Comprehensive QA for radiation oncology report of AAPM Radiation Therapy Committee Task Group 40", Med. Phys. 21, 1994, pp 581), as well as the imaging system involved in the planning and which may be used during treatment with image guided radiotherapy (IGRT), and the fundamental processes of the mechanical setups and alignments that are required in the delivery room. The elements extend even further than this when considering the personnel, servicing, and software updates to the systems in planning and control. Such an elemental approach may be ideal but is also impractical in its administration and management of results.

Current approaches rely on validating sub-parts of the system with hopes of detecting sources of error that would affect the dose planning and delivery system as a whole. It is good to hone different QA tests to probe defined sub-systems. However, often these approaches are limited in that they may not guarantee that "good results" correlate with accurate dose to the patient nor do they project how "bad results" correlate with unacceptable dose to the patient. That is, the impact to the patient dose system is not quantified by the sub-system test. For example, a popular sub-system approach over the past eight years has been the dose map measurement on a QA phantom and the comparison of the measured to the planned dose map on that phantom. (see "MapCHECK" and "EPIDose" as described at www.sunnuclear.com and manufactured by Sun Nuclear Corp, Melbourne Fla.). This test method using MapCHECK™ or EPIDose™ provides a verification of the system's ability to deliver the patient's treatment plan on the QA phantom. First, the patient planning process is completed, which includes a treatment plan delivery from the radiation machine and a 3D dose distribution in the patient anatomy. Next, the TPS computes the dose in the QA phantom using the patient's treatment delivery plan. Then the measurement of the dose map in the QA phantom is made with the patient's treatment delivery plan and compared to the TPS computed dose in the QA phantom. Differences between the measured and planned map are errors caused by either delivery errors or dose computation errors. Such dose distribution errors may then be expected in the patient anatomy; the significance of the error to the treatment outcome is a judgment made by the clinician, aided by the comparison criteria, but generally without guidance of how the 3D dose to the patient or DVH changed due to the detected error.

One method does not involve a measurement; instead, the TPS plan for beam shaping is used in the calculation of the planned dose map on the homogeneous QA phantom, using a dose model algorithm that has been validated by a measuring device, such as the MapCALC™ product by Sun Nuclear (see "MapCALC" at www.sunnuclear.com and manufactured by Sun Nuclear Corp, Melbourne Fla.). The dose map comparison is made to the TPS dose map calculation on the QA phantom, very much like in the MapCHECK™ measurement comparison described above. This comparison method may be suitable as long as there is a comprehensive measurement QA program on the machine delivery itself, and periodic comparison of the MapCALC™ dose map to the measurement dose map. If there are errors in the dose map comparison, the errors signify differences in the dose modeling between the TPS and MapCALC™. The clinician is not aware of the impact of the error on the DVH, i.e., is the error serious enough to investigate?

Other treatment plan QA validation methods seek to achieve QA by DVH estimation and subsequent comparison to the plan. They have been generally far more complicated because of their dose modeling in the heterogeneous structures of the patient. There are basically two categories, those that assume accurate delivery by capturing the planned beam fluence by various methods, (see Joseph O. Deasy, et al, "CERR: A computational environment for radiotherapy research," Med. Phys. 30, (5), May 2003, 979) and those that measure, or nearly measure, the beam fluence (see U.S. Pat. No. 6,853,702 to Renner for "Radiation Therapy Dosimetry Quality Control Process"). Both calculate the dose to the patient from the beam fluence using a dose algorithm that is independent from TPS patient dose calculation. The dose modeling in the QA systems may be similar to or significantly different from the TPS dose modeling. After patient dose calculation, the QA system will then summarize the dose into a DVH analysis for the clinician. Without even considering the accuracy of the assumed or measured beam fluence, the fundamental problem is the confidence in dose modeling; there are now two dose models in competition, both computing a 3D dose distribution in the patient anatomy and summing the dose to create the DVH of interest. The clinician is faced with a decision as to which is correct if there is a significant difference. Furthermore, if the TPS has been rigorously commissioned prior to use, why would the clinician decide in favor of another less rigorous dose model? A TPS should be commissioned (via data entry, beam modeling, etc.) to be as accurate as it can possibly be, and once this is complete, consistency should be the rule, i.e. by using defined and validated processes, maintaining the performance, and quantifying and understanding its inherent limitations.

SUMMARY

The present invention provides a method, wherein one embodiment may be provided as herein referred to as Plan Dose Perturbation (PDP™), that utilizes a QA phantom with a plurality of radiation detectors, optionally arranged in a detector array, and comprises means to analyze the detector response to create a dose map of sufficient spatial density that allows it to be compared to the TPS dose map as calculated in the QA phantom with the patient's treatment delivery plan, with such comparison resulting in a dose correction map that is manipulated mathematically to generate a 3D dose error grid for the respective sub-set of beams/segments, and which is applied onto the TPS dose map, as calculated in the patient anatomy with the patient's treatment delivery plan, where such application of correction map is by perturbing the original TPS calculation grid for that sub-set of beams/segments and then doing this until all estimated perturbations in dose from all sub-beams/segments have been accounted for. The resulting corrected dose map is akin to a "virtual measurement" that is extended to three dimensions inside the patient anatomy, but without having to calculate dose from first principles, thus without needing an independent dose calculation algorithm.

One method aspect of the invention includes determining a patient dose during or prior to therapy from an external radiation beam. The method includes measuring a dose distribution from a patient plan as delivered in a QA phantom at each of a plurality of beam angles and comparing the measured dose distribution at each beam angle to a corresponding treatment planning system (TPS) dose modeled distribution in the QA phantom, with the comparing resulting in a correction distribution that when applied to the TPS dose modeled distribution results in the measured dose distribution. A dose error kernel for sub-beamlets of the radiation beam is generated based on the determined dose distribution, and the dose error kernel is geometrically applied from the source through a volume that equals the TPS dose volume for a patent beam for each beam angle. The correction distribution is then applied to the TPS patient dose volume for each beam angle for providing a corrected dose distribution in the patient for each beam angle.

Another method aspect of the invention includes a measurement is made and compared to a TPS dose map, resulting in a dose error map in the QA phantom in the specific plane of measurement and at the detector locations in a MapCHECK process, by way of example. When the dose error is applied to the original TPS dose plane, the result reconstitutes the measured dose plane. Note that the TPS dose rays are not fluence ray tracing but are modeled dose values in the patient anatomy, as calculated by the TPS dose modeling at the time of treatment planning. Dose correction kernels following the ray tracing are then be applied to the respective TPS dose rays, regardless of the phantom composition, resulting in a corrected 3D dose distribution in the patient anatomy without involving any dose modeling in the calculation. This perturbation, as defined in the following paragraphs, allows dose corrections in the patient anatomy without needs of beam modeling, beam fluence, patient imaging/density, or dose calculation algorithm.

Yet another method aspect may comprise measuring a dose distribution from a patient plan as delivered in a QA phantom at each of a plurality of beam angles and comparing the measured dose distribution at each beam angle to a corresponding treatment planning system (TPS) dose modeled distribution in the QA phantom, with the comparing resulting in a correction distribution that when applied to the TPS dose modeled distribution results in the measured dose distribution. The correction distribution is then interpolated to non-measured points for each beam angle and the interpolated correction distribution is geometrically projected toward the source of radiation through a volume that equals a dose volume of the TPS for a patient beam for each beam angle. The interpolated correction distribution is then applied to the TPS patient dose volume for each beam angle for providing a corrected dose distribution in the patient for each beam angle.

By way of example, the method may be described in specific detail with the MapCHECK™, a measurement is made and compared to a TPS dose map, resulting in a dose error map in the QA phantom in the specific plane of measurement and at the detector locations in the MapCHECK™. When the dose error is applied to the original TPS dose value, the result constitutes the measured dose plan. The TPS dose calculation results from a dosimetry model that has been commissioned by the clinician. Since we know the detector location in (x,y,z) coordinates with respect to the radiation source, the dose correction factor at each detector location can be applied to the TPS dose rays intersecting the detector and the target. Note that the TPS dose rays are not fluence ray tracing but are modeled dose values in the patient anatomy, as calculated by the TPS dose modeling at the time of treatment planning. The dose correction kernels following the ray tracing can then be applied to the TPS dose rays, regardless of the phantom composition, resulting in a corrected 3D dose distribution in the patient anatomy without involving any dose modeling in the calculation. This perturbation, as defined in the following paragraphs, allows dose corrections in the patient anatomy without needs of beam modeling, beam fluence, patient imaging/density, or dose calculation algorithm.

The example above illustrates a Perturbation of a Modeled Dose—perturbation theory is an approximation technique for treating functions that do not have a known closed solution (see Robert M. Eisberq, "Fundamentals of Modern Physics", Ch 9 Perturbation Theory, John Wiley & Sons, 1967). In perturbation of a modeled dose, we have
- a 3D dose function in the TPS that has been approved for treatment, i.e., unperturbed planed dose $D(x,y,z)$
- a delivery system or TPS modeling error that perturbs the planned dose function, i.e., perturbation operator "$d(x,y,z)$"
- a QA phantom measurement of the dose delivery that results in a 3D correction technique that allows an approximate solution to the 3D perturbed dose $D'(x,y,z)$, i.e., that which was delivered.

Hence we get a good approximation to the solution of the plan dose that has been perturbed, i.e., Plan Dose Perturbation (PDP).

Further discussion points on perturbation:

a) We are developing a good approximation to the solution of the perturbed dose D'(x,y,z), which is the delivered patient dose whose exact value is generally not easily determined b) This is being done in terms of the perturbation d(x,y,z), where d(x,y,z) is a modeling error in the TPS or a leaf sequence error in the delivery, or any combination of errors and conditions that may affect dose delivery. The effects of the perturbation on the "known" unperturbed dose D(x,y,z) are measured, resulting in measured dose M(i,j,k) which is a subset of the D'(x,y,z) at specific measured points. We, do not know the exact nature of the perturbation function d(x,y,z), but can calculate corrections at specific points, M(i,j,k)/D(x,y,z), and interpolate these corrections to the dose structure. It is of interest to note the M (measurement) is in a phantom and therefore the volume may be different. The relationship of Dphantom(i,j,k) and Mphantom(i,j,k) is used to generate a 3D perturbation function (per beam), defined as d(x,y,z). Then d(x,y,z) is applied to D(x,y,z) to yield D'(x,y,z), the estimated/corrected dose. This can then be used to visualize dose differences in the patient and to show the corrected DVH statistics vs. the unperturbed (planned) DVH statistics.

c) Unperturbed dose means TPS calculated dose to patient.

d) Perturbation means a dose delivery error caused by any function that creates a discrepancy in the calculated dose, such as modeling error, leaf sequence error, compensator error, and the like.

e) Example errors that are not perturbations, i.e., not a minor disturbance, would be things like an incorrect TPS plan file for the MLC, an alignment error, and the like. These are like binary errors, either correct or incorrect. They will be caught by the measurement, but would not generally be used to calculate the perturbed dose. An MU error could be used to calculate the perturbed dose, but the error would still need to be corrected since it was global across the entire field.

The uncertainty of PDP corrections will depend upon the magnitude of the error itself and the initial accuracy of the TPS calculated (i.e. unperturbed) dose. Therefore, this perturbation method is qualified to correct for typical errors detected in complex radiation therapy QA for commissioned systems, but it is not qualified to correct for grossly inaccurate TPS calculations. It may seem reasonable to place an error limit on the perturbation method; it is also reasonable to expect that the clinician will not use a treatment plan when the QA results show large errors that may not justify perturbation analysis, but instead indicating that there is a justified need to re-plan the treatment and not examine the impact of the DVH that had been accepted for treatment. For example, if the perturbation correction has an uncertainty in a heterogeneity region of 10%, and the correction itself is 10%, then the resulting error in the corrected dose is 10% of 10%, or 1%. These limits will grow from the experience of this application but in no manner limit its usefulness under appropriate conditions.

PDP has been simulated for both homogenous and heterogeneous media which are much simpler than a patient but yet qualifying and demonstrating. A baseline beam of $10 \times 10$ cm$^2$ 6 MV open field was measured with MapCHECK™. Then, "error-induced" beams were created by applying aluminum disks that induced four different error levels: ~3%, ~7%, ~14% and ~18%. These error-induced beams were measured with MapCHECK™. 2D dose error maps were derived by comparing the baseline beam and the error-induced beam at 5 cm QA phantom depth, 100 cm SSD. Then, for each error level, the correction maps were applied on ray tracing from source to detector to estimate dose values at depths of 1 cm, 2 cm, 10 cm and 20 cm. These corrected dose values were compared with actual dose measurements at corresponding depth. Comparisons between PDP corrected and actual measured dose maps resulted in a maximum percentage difference of less than 1% over all tests. The PDP method demonstrated its ability to measure and correct dose errors in a heterogeneous volume. Changes in projected errors with varying depth will be handled with a 3D perturbation kernel generated by physics modeling tools.

In the Background section of this specification, the patent to Renner[6] was referenced for providing a method that employs a measurement on a QA phantom that leads to a re-calculation of the patient dose which is then comparable to TPS patient dose. While the Renner method may appear to be similar to the PDP method herein described as one embodiment of the invention, there are very significant differences as clearly seen when both are examined in full detail.

Other methods of reconstructing dose based on fluence (as described in T. R. McNutt, T. R. Mackie, P. J. Reckwerdt, B. R. Paliwal, "Modeling Dose Distributions from Portal Dose Images Using the Convolution/Superposition Method," Med. Phys. 23(8), 1996; T. R. McNutt, T. R. Mackie, B. R. Paliwal, "Analysis and Convergence of the Iterative Convolution/Superposition Dose Reconstruction Technique," Med. Phys. 24(9), 1997; and Mathilda van Ziitveld, Maarten L. P. Dirkxa, Hans C. J. de Boera and Ben J. M. Heijmen, "3D dose reconstruction for clinical evaluation of IMRT pretreatment verification with an EPID," Radiotherapy and Oncology, 82(2), February 2007, Pages 201-207) estimations derived from measurements have been described, but Renner is herein selected by way of example for a clear understanding of distinguishing features if the present invention and embodiments herein presented. Consider known methods and systems as represented by Renner by way of example. Renner teaches a radiation therapy machine having a gantry mounted radiation source for producing a plurality of radiation beams directed toward a patient at selected gantry angles, the beams including a plurality of absorbing devices to shape and modify the intensity across the beam, the process of verifying the dose delivered to or to be delivered to the patient from a plurality of such beams consisting of the steps of: (a) *measuring the output of each such intended treatment beam over the area of the beam in a plane perpendicular to the central ray of the beam using a pre-patient detector prior to impinging upon the patient*, (b) using said measured output of each beam to calculate the dose to the patient from the beam using a dose algorithm, (c) accumulating the dose to the patient from all such treatment beams to produce a dose distribution, (d) using said dose distribution to compare to the intended dose to verify the correctness of the treatment. The above Renner teachings highlighted in italics are generally generic to radiation oncology and have been for a decade or more. The bold accent is added for clarity.

With attention now to embodiments of the present invention, and without repeating the underlined text above, but understanding that is indeed how the PDP method may begin, the invention teaches (b) comparing the measurement to a treatment planning system (TPS) dose map, resulting in a correction map in the QA phantom. The correction map is then applied, employing ray tracing to conform to beam divergence and to allow changes of the error function with depth. This correction algorithm does not recalculate dose (i.e. does not account for energy spectra, estimate attenuation, generate TERMA, simulate dose deposition kernels in media, and the like. Such modeling was originally performed (correctly or incorrectly) in the original TPS dose algorithm. The PDP dose distribution is not a result of a new dose algorithm, which would again need measurement verification, but instead it retains the TPS dose model with an accuracy improvement from the measurement correction map, (c) accumulating the dose to the patient from all such treatment beams to produce an accumulated 3D dose distribution in the patient anatomy, (d) using said dose distribution to compare to the intended dose to verify the correctness of the treatment.

The notation "correctly or incorrectly" implies an important concept and needs further explanation. As stated earlier, the TPS is commissioned for treatment planning and is a vital part of the radiation oncology program. The dose calculation in the TPS is relied upon to make decisions on effective treatment. It is also known that TPS systems are not perfect; it is the clinician's responsibility in the commissioning process to verify the calculations and understand the situations in which these calculations are not accurate. These situations come in two categories, beam shapes that are difficult to model in homogeneous media and heterogeneous media that are difficult to model in particular beam shapes. Both categories can exist in a patient plan, some beam shapes are avoidable but most heterogeneities are not avoidable. The measurement of difficult geometries in a homogeneous media have the potential to correct the TPS dose modeling errors in the PDP Method, as well as delivery errors, but a measurement in a homogeneous media will not be able to correct TPS heterogeneities errors unless the QA phantom is designed for such measurements.

By way of further explanation, consider a "prior art tailor" dealing with a man who walks into a department store and purchases a suit according to the size labeled on the suit. He puts the suit on. The prior art tailor measures the fit and uses the measurements to make a new suit with new fabric. Is there a need for the man to try the new suit on? Of course, it's a new suit.

Now consider a "PDP tailor" with a man who walks into a department store and purchases a suit according to the size labeled on the suit. He puts the suit on. The PDP tailor measures the fit and finds the adjustments (i.e., corrections to the suit fit) by marking the suit on the man. The suit is removed. The PDP tailor makes the alterations to the markings (i.e., corrected). Is there a need for the man to try the new suit on? This alteration method clearly works for small corrections without the need to try on the suit again.

The reasons for the analogy are that dose algorithm is a rather abstract concept and the methods employed by known techniques, such as Renner, herein presented by way of example, and PDP to achieve the final goal of finding the correct dose distribution may seem blurred to someone not trained in the art. However, the fact that Renner uses a dose algorithm to re-compute the dose distribution instead of applying a correction map to the original TPS dose algorithm is very significant. The objective is to remove the inaccuracies of dose algorithms that are inherent in the planning systems. A measurement determines these inaccuracies, but the application of another dose algorithm will simply introduce additional inaccuracies which beg measurement as much as the original TPS dose algorithm.

Consider outcome differences between Renner and the present invention, again herein referred to as PDP. There are two sources of error (relative to the planned or expected dose) in a treatment delivery. They are dose modeling errors in the TPS dose algorithm—modeled on a planned delivery of beam modulation. There are delivery execution errors with respect to planned beam modulation. While Renner determines errors, there is no method of assigning these errors to delivery or TPS dose algorithm.

However, there is a significant difference between the Renner and PDP methods in applying these measured errors for their intended use.

The Renner method seems to assume the errors are due to delivery error, i.e., he measures the dose, converts it to some "fluence" and then employs his dose algorithm to calculate the dose to the patient. This is similar to what the TPS does, it models the fluence per the expected beam modulation, and then it calculates the dose from fluence using a dose algorithm. So the outcome of the Renner method has the potential of introducing new Renner dose algorithm errors albeit different from the TPS dose algorithm errors. Renner does not mention anything about comparing the original dose measurement to the Renner dose algorithm dose (see D. W. O. Rogers, "Monte Carlo Techniques in Radiotherapy," Physics in Canada, Medical Physics Special issue, 2002, v. 58 #2, pp 63-70). He cannot in his system because he measures the dose in a QA phantom and then reconstructs the dose in the patient; he should first reconstruct the QA dose using the Renner dose algorithm, and then compare to the QA measurement. This would be a true test of the dose modeling in the Renner dose algorithm. This fact is the fundamental weakness in the Renner patent.

The PDP method does not employ an estimated delivered "fluence"; nor does PDP assume the source of error. Rather, PDP uses an assayed "Delivered vs. Planned" measurement (which includes both sources of error) that is used to correct the original TPS dose algorithm patient dose; the result of which is a dose distribution that has correction for delivery and TPS dose algorithm errors, and does not introduce any dose algorithm errors of its own because it does not employ a dose algorithm to re-compute the dose. Unlike the Renner method, there is no need to reconstruct the TPS QA dose in the PDP method because it does not re-compute dose. It uses the measured QA dose to derive the correction map. If it uses the correction map to reconstruct the TPS QA dose, the result is that it gets back the measured QA dose. This fact is the fundamental strength in the PDP method, i.e., no additional errors are introduced.

The application of the correction from measurement (the PDP Method) is closer to a measurement in the patient, which is the goal. The Renner Method is simply a second dose calculation in the patient.

It should be clear that the only difference in the Renner claim and the PDP method lies in the interpretation of dose algorithm in part b of claim 1. It should also be clear that dose algorithm is a complex term that needs definition and cannot ride on the unskilled interpretation of any calculation being an algorithm, no matter how simple. Look into the Renner patent teaching to define dose algorithm.

Consider specific teachings from the Renner patent reference.

1. "Software like a treatment planning system is then used to compute the dose to the patient for comparison with the intended treatment prescription."

This is a clear reference to the anticipated features of the dose algorithm, i.e., like a TPS.

2. "The measured beam intensity is then used with conventional and known computational methods to compute the dose to the patient achieving an accuracy near that of the original treatment plan."

Again, this is a clear reference to the anticipated features of the dose algorithm. Furthermore, the PDP method of dose structure correction is not a known computational method. It has never been used before.

3. "The measured field images are then used to recompute the dose distribution in FIG. 3 to the patient using anatomical cross sectional images of the patients body and a dose algorithm."

This is a clear reference to the need for anatomical images of the patient in the dose algorithm, as would be used in a conventional TPS. Without anatomical images, a TPS is useless. This leads us to the uniqueness of the PDP method, that there is no need for anatomical images to recompute the dose to the patient.

4. "The process described below is for the purpose of verifying and testing the intended treatment plan . . . It is assumed that . . . These techniques generally involve obtaining cross sectional images of the patient's body in FIG. 2 with CT scanners or other means, and generating a treatment plan using computerized treatment planning systems provided for that purpose. CT is generally the imaging modality preferred due to its geometric accuracy and that CT pixel numbers can be converted to electron density needed by dose algorithms."

This is a clear reference to the needs of the dose algorithm. Here Renner assumes cross sectional images of the patient, such as would be obtained from a CT scanner, are available to the dose algorithm, and that CT pixel numbers can be converted to electron density needed by the dose algorithm. The PDP method does not use nor need the CT images nor the electron density numbers.

5. "The software system then reads in the CT scans or other cross sectional images that were used in the treatment planning process."

Again, a clear reference to the anticipated CT scan like images that are used by the Renner dose algorithm.

6. "A dose algorithm provided in the software system then computes the dose distribution to the patient in the same manner that a treatment planning system does except that the input and specification for the fluence for each field comes from the above measured field images"

Yet another clear reference to the anticipated features of the dose algorithm. This one points out that Renner method supplies the dose algorithm with a fluence calculated from the measured dose rather than a derived plan fluence in a typical TPS. Otherwise, the dose algorithm is same as would be in a TPS. Furthermore, the measured dose values are clearly available and could have been used to correct the TPS dose values, but Renner clearly teaches converting the dose to fluence which introduces more uncertainty into the method.

7. "The particulars of the dose algorithm employed in the software are not important here as any algorithm may be employed that is capable of using a measured field fluence derived from dose to compute the dose. We are using a pencil beam algorithm that is typically employed by radiation therapy treatment planning systems. The pencil beam algorithm is well known in the radiation therapy journal literature."

This passage is very specific to the needs of the dose algorithm; Renner states that its "particulars" are not important as long as it is capable of using a measured "field fluence". The PDP method does not use a measured "field fluence", it uses a correction error map that is derived from a measured dose map. The error map is not by any stretch of the imagination a "field fluence".

8. "Relative monitor units are then used to normalize the weight of these small subunits of the applied field. The dose to the patient is then computed from the sum of the dose contribution from all such subunits that make up the applied radiation field and this part of the algorithm is no different from that typically employed by treatment planning systems."

This is a clear reference to the anticipated methods in the dose algorithm. The small subunits are in reference to the pencil beam algorithm, specific to the Renner dose algorithm method and generally common to TPS dose algorithms. The PDP method does not use a pencil beam feature nor a TPS dose algorithm.

The next citation does not specifically relate to the anticipated requirements of the dose algorithm, in as much as its connection through common errors to TPS.

9. "False negatives may be possible due to common errors in both the verification system described here and the treatment planning and delivery system, but we have significantly reduced the number of common variables by starting with a measured field at instead of modeling the radiation field which the planning system typically does."

Here Renner does identify the fact that his method, "the verification system", and TPS and delivery system can produce common errors. He was close to identifying the weakness in his method, but did not identify the possibility of using the Renner method to calculate the QA dose prior to calculating the patient dose. If he would have done this, he could have identified a method of validating the dose algorithm that will be used to calculate the patient dose.

As pointed out above, the Renner method has no option for convergence to the correct answer. If a QA dose is recalculated prior to the patient dose and compared to the measurement, and if the new dose does not agree with the originally measured dose, there is no method offered or suggested on improvement. Yet possible errors are admitted in the verification system and that these errors can be common to the TPS. Of course they can, both the TPS and the Renner system use conventional and "common" dose algorithms, as described in the above.

As addressed in the above references application Ser. No. 61/035,834 filed for "Three Dimensional Dosimetry Using Solid Array Geometry," the disclosure of which is herein incorporated by reference, the dose measurement by the detectors in the field is a direct measurement of the radiation dose delivery, as it enters the cylindrical array and as it exits the cylindrical array. The difference in comparison can be used to calculate the error and subsequent correction factor that can be applied to the intended 3-D dose map, resulting in a corrected 3-D dose map of the radiation delivery.

Many aspects of the treatment plan and delivery process have not been discussed, such as the multiple treatment fields that are the nature of radiation therapy. Each of these fields will have a dose calculation that adds to the total dose in the patient. Depending upon the treatment modality (Conventional blocked fields, Intensity Modulated Radiation Therapy, Arc Delivery, VMAT, Rapid ARC, HI-ART, SAT, CyberKnife robotic delivery, the nature of the QA phantom geometry may be planar or 3 dimensional, but the concept remains the same. "Rapid Arc" is by Varian, Palo Alto Calif.; "HI-ART" is by TomoTherapy, Madison Wis.; "VMAT" is by Elekta, Crawley UK; "Single Arc Therapy (SAT)" is by Siemen, Germany; and "CyberKnife" is by Accuray, Sunnyvale, Calif. What has been discussed in this embodiment is applicable to most if not all external beam radiotherapy delivery techniques.

The detector spatial density in the QA phantom will influence the method of correction factor generation. Ultimately the correction factor spatial density should be close to the dose array spatial density that is used to construct the DVH or other clinical QA analysis techniques that are used to judge the adequacy of the treatment plan. With film and EPIDs, the detector spatial density often exceeds the TPS dose grid density, making the correction matrix of sufficient density that evaluations corrections can be immediately applied along the dose ray tracing without further need of higher correction matrix density, which may mitigate the need of interpolation on the initial QA correction matrix that results from the comparison the TPS QA dose map. Further to this and as discussed earlier in the Background, it is possible to achieve near measurement accuracy in QA Phantom geometries with calculations methods such as MapCALC[4] or Monte Carlo[9] (where Monte Carlo techniques for radiation transport in materials are described and several examples of their use in modern radiotherapy dosimetry and treatment planning are presented). It is then reasonable to extend the PDP method to include these accurate calculation methods when demonstrated to be equivalent to measurement in a QA phantom as a substitute for the measurement.

With MapCHECK™, which has a detector spatial density of 7.07 mm between detector neighbors in the 10×10 cm array, the correction factors at the detector points will require an interpolation technique to achieve a higher density, for example, 1 mm grid on the correction map at the measurement location. There are various methods of interpolation that may be used. The methods may be dependent upon the neighboring dose gradients, following dose contours, or morphing the TPS dose map shape onto the sparse correction factor map while compensating the TPS dose map shape for the corrections and the distance to agreement in high gradient regions. With such a priori information from TPS, intended dose distribution becomes a powerful tool to extend the detector density without too much sacrifice on accuracy.

The detector array geometry in the QA phantom will influence the method to ray trace correction factor. A 2D planar array will be oriented with the beam axis normal to detector plane, therefore ray tracing of off axis correction factors is accomplished by planar geometry. A 3D array may have the added benefit of predetermining the beam angle by ray tracing beam edges or beam shapes through the solid geometry formed by the array, even though the array itself may be a cylindrical shell. The correction factors derived on the 3D array can then be ray traced through the 3D TPS patient dose map by using the predetermined beam angle information.

BRIEF DESCRIPTION OF DRAWINGS

A preferred embodiment of the invention, as well as alternate embodiments are described by way of example with reference to the accompanying drawings and photographs in which.

DESCRIPTION OF EMBODIMENTS

The present invention will now be described more fully hereinafter with reference to the accompanying drawings, in which embodiments of the invention are shown. This invention may, however, be embodied in many different forms and should not be construed as limited to the embodiments set forth herein. Rather, the embodiments herein presented are provided so that this disclosure will be thorough and complete, and will fully convey the scope of the invention to those skilled in the art.

Figure 1:
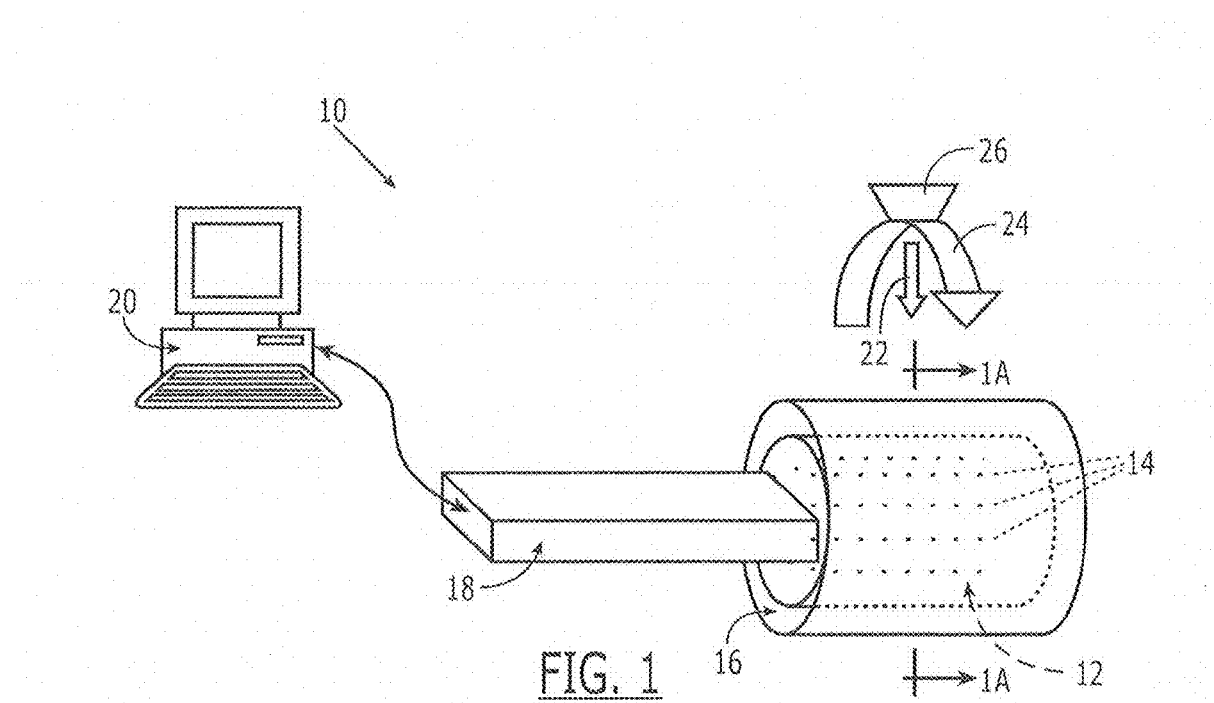
FIG. 1 is a diagrammatical illustration of a QA phantom 3D cylindrical array system.
Figure 1A:
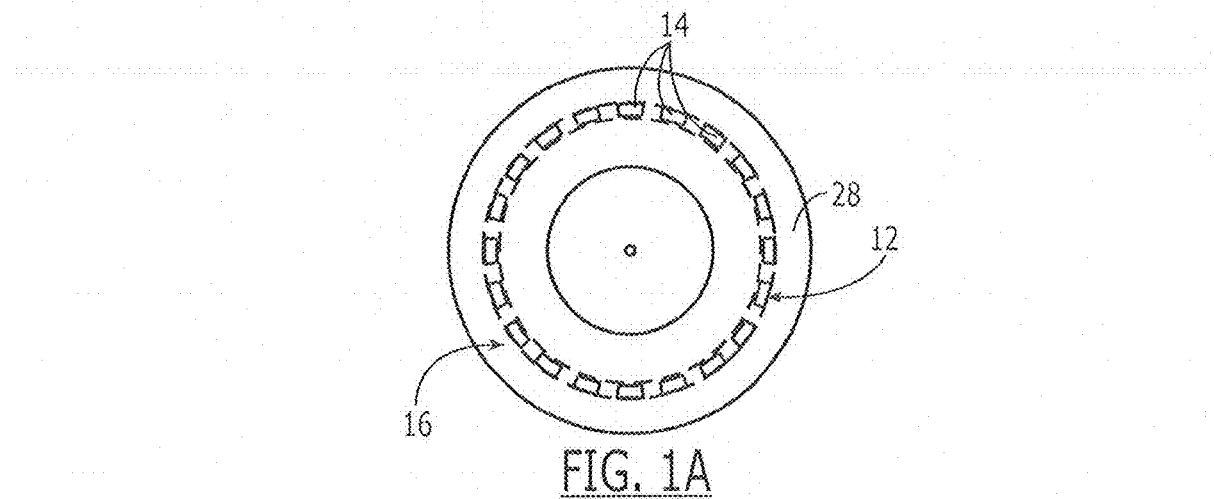
FIG. 1A is a partial cross sectional view of FIG. 1 taken through lines 1A-1A.

By way of example, and with reference initially to the schematic diagram of FIG. 1, one embodiment of a dose measurement QA phantom system 10 in keeping with the teachings of the present invention may comprise a cylindrical array 12 of radiation detectors 14 with the array concentric with a cylindrical phantom 16. Electronics 18 and processor 20 operable there with are capable of analyzing and simultaneously recording a response of the radiation detectors 14 at a measurement frequency sufficient to capture dose delivery 22 at given time or angle segments 24 from a radiation system gantry 26. The detectors 14 are arranged in a repeating and predictable geometric pattern 28, such as illustrated with reference to FIG. 1A, making it possible to know there spatial position in a radiation field as illustrated with reference to FIG. 2 for the cylindrical array 12 and FIG. 3 for a plane array 30 that is kept normal to a beam axis.

By way of further discussion regarding the system 10, and with reference again to FIG. 2, an axial view of the system is illustrated in a line drawing, wherein the radiation source S 32 from the gantry 26 is rotating around a center C 42, with 4 different time segments 24 indicated as examples at source positions $S_1, S_2, S_3, S_4$. The cylindrical detector array 12 also illustrated as $D_n$ is also shown and is concentric to the rotation of the source 32. The illustration is not drawn to scale for clarity. Only one radial array 12 of detectors 14 (i.e. one pass around the cylinder circumference) is shown. The radiation beam 36 from the source 32 is limited by blocks or leaf pairs 38 (A and B). A beam edge 36a for each position is shown as $(A_1, B_1), (A_2, B_2), (A_3, B_3), (A_4, B_4)$. One can think of this illustration as sampling the radiation fields defined by one leaf pair 38 of an MLC leaf bank of a LINAC. The radiation field 40 passing through each leaf pair 38 is passing through the cylindrical array $D_n$ 12 and designated as $F_1, F_2, F_3, F_4$. It is observed that the field width 40a changes as the source 32 rotates. The independent movement of leaves in each leaf pair 38 allows the placement of radiation virtually anywhere allowed by the range of movement of the leaves, including fields that may not pass through the center as herein illustrated for $F_3$. Regardless of the orientation of the source 40, the field of radiation 46 enters the cylindrical array 14 $D_n$, passing near some detectors 18 and exits the cylindrical array $D_n$ while passing near other detectors. With a well ordered array geometry, and with a prior knowledge of the penumbra transfer function of the detector response to the beam edge shape caused by the leaf pair, it is possible to re-construct the source position for a measured field of radiation.

Figure 2:
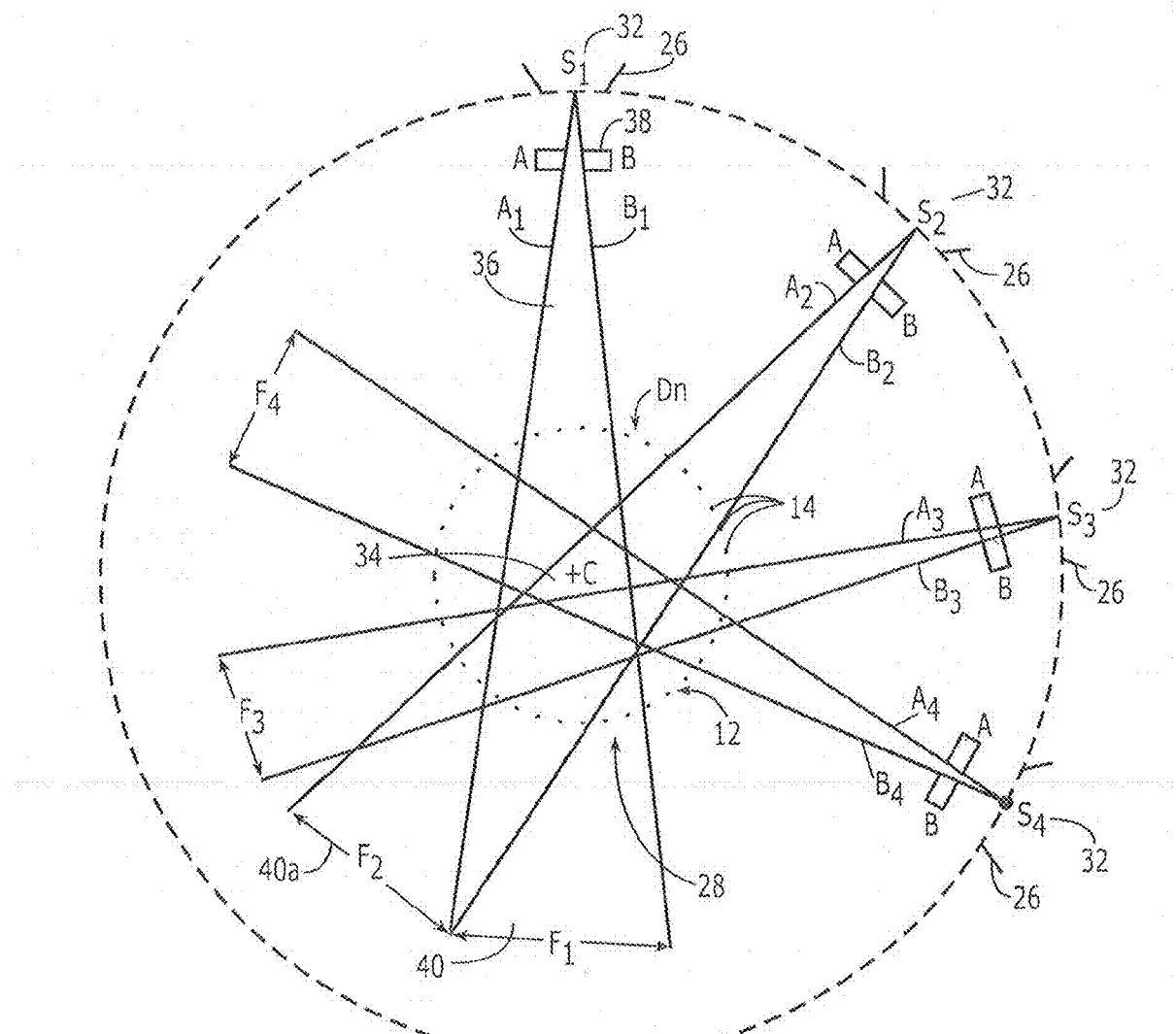
FIG. 2 is a diagrammatical axial view of the system of FIG. 1.
Figure 3:
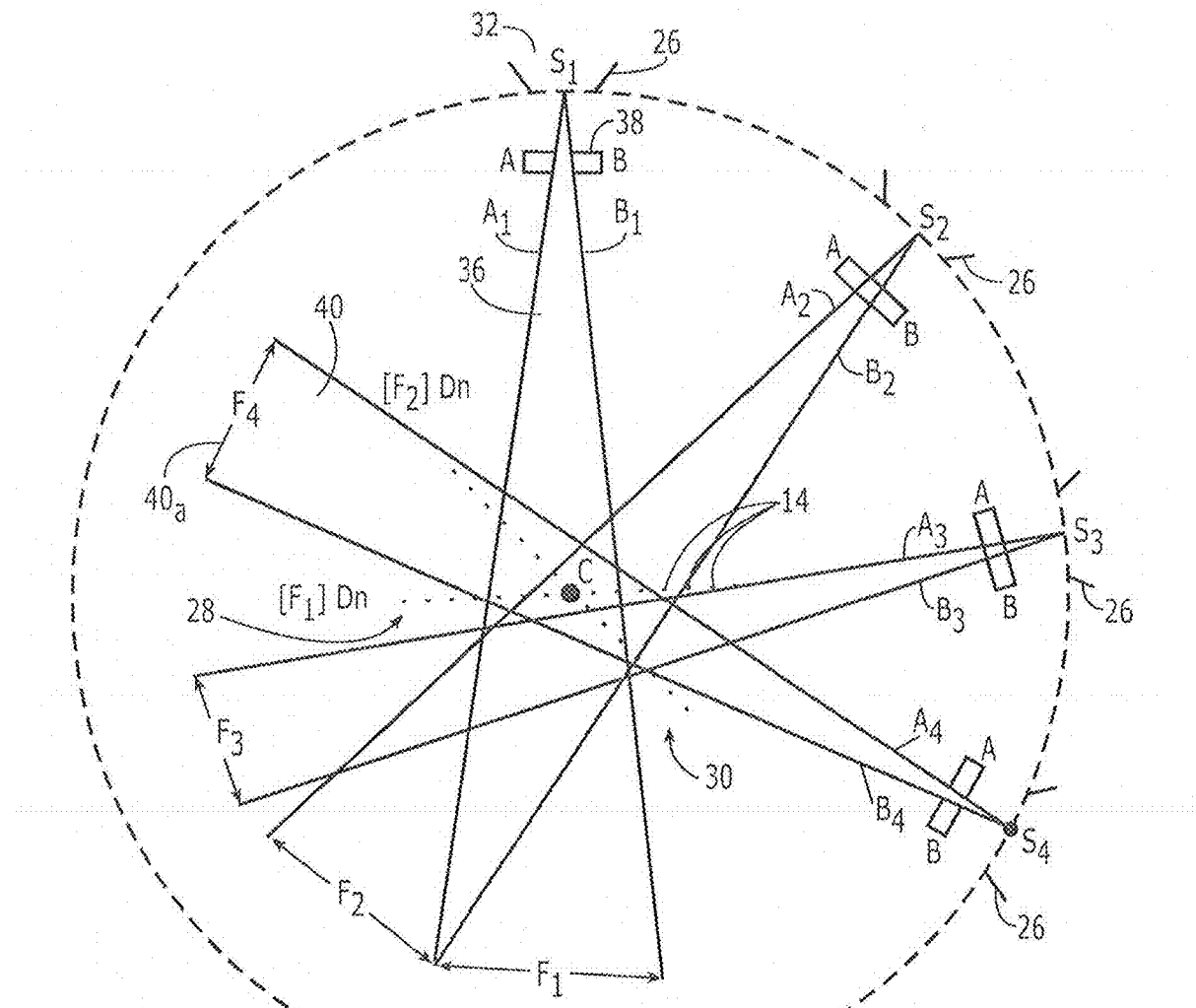
FIG. 3 is a diagrammatical illustration of a 2-D detector plane QA Phantom, where the detector plane stays perpendicular to the radiation field.

As above described, with the detectors 14 arranged in a repeating and predictable geometric pattern 28, it possible to know there spatial position in a radiation field 40 as illustrated with reference to FIG. 2 for the cylindrical array 12 and FIG. 3 for a plane array 30 that is kept normal to a beam axis.

Figure 4A:
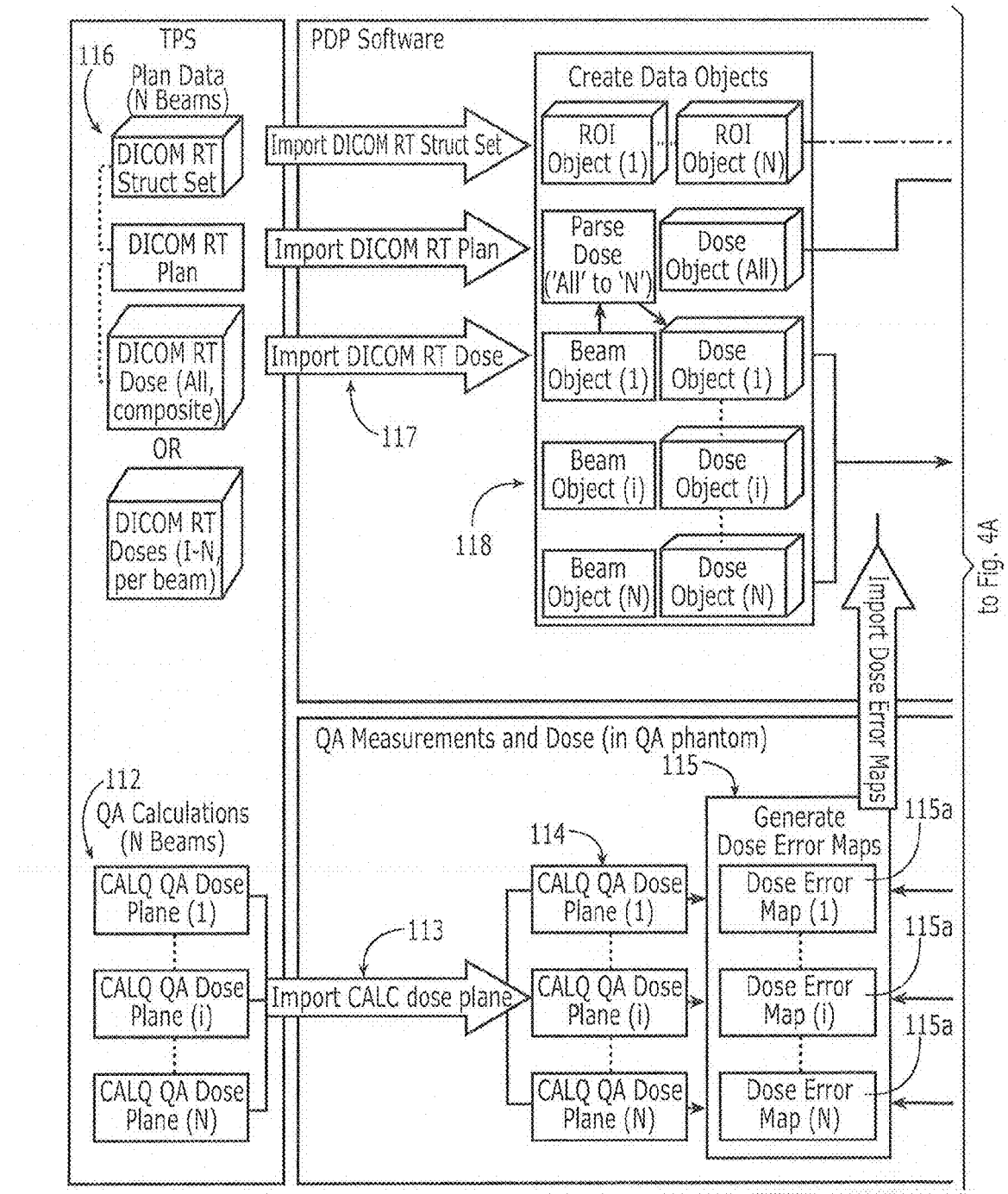
FIGS. 4A and 4B are combined to present a diagrammatical illustration of one Plan Dose Perturbation (PDP) method in keeping with the teachings of the present invention.
Figure 4B:
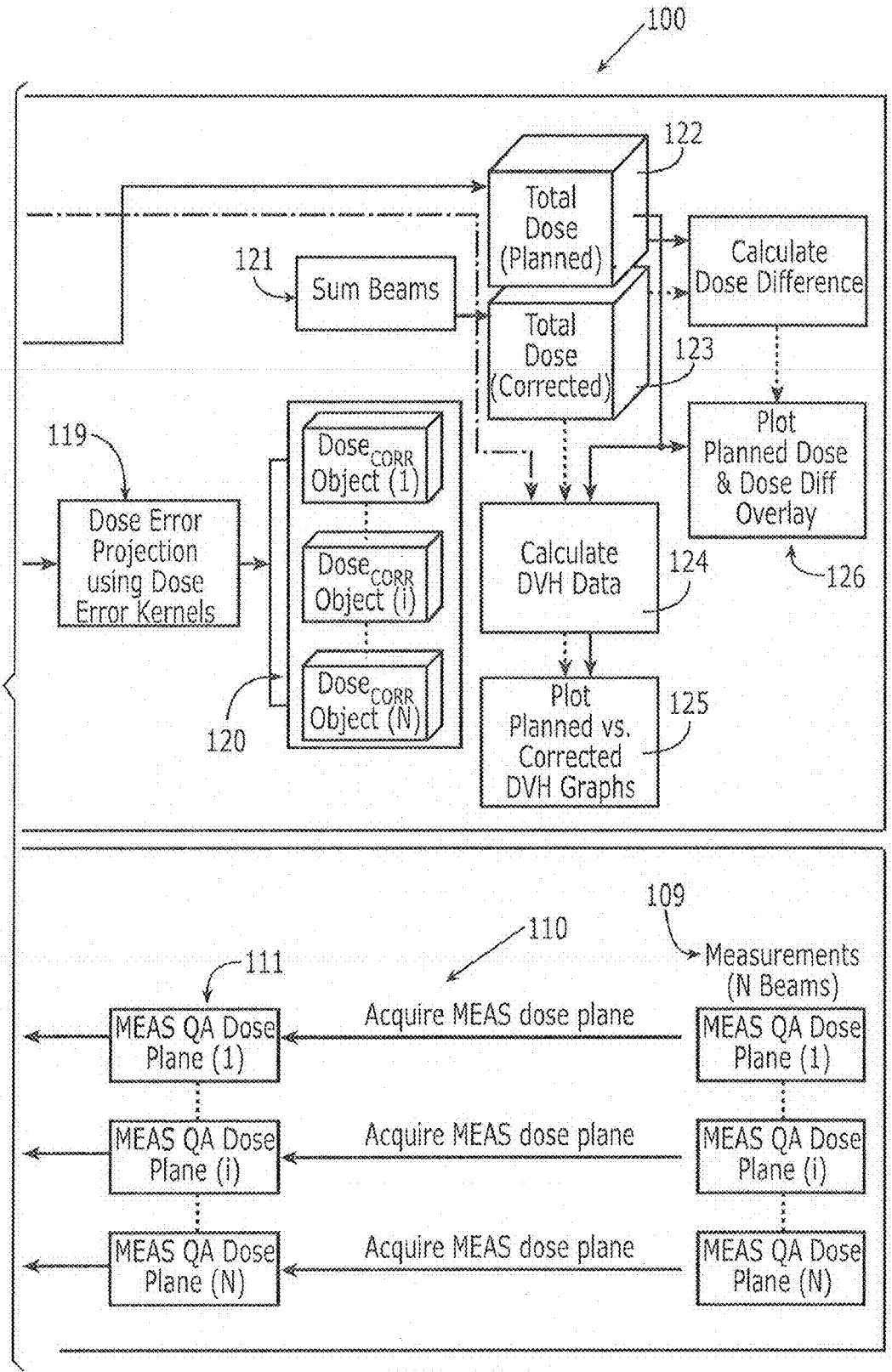

One embodiment of the present invention is directed to a method, herein referred to as a PDP process or method 100, and schematically represented with reference to FIG. 4. As illustrated with reference to FIG. 4, one embodiment comprises a QA phantom dose map measurement 109 being imported 110 into an analyzer 111 and a TPS QA dose map calculation 112 imported 113 into an analyzer 114, where the dose maps from the measurement 111 and TPS 114 are compared 115. The errors in the comparison 115 result in a dose correction map 115a for each radiation field.

With continued reference to FIG. 4, the TPS patient 3D volume dose maps for each radiation treatment field 116 are imported 117 into the analyzer as Dose Data Objects 118 and each Object is corrected with the Dose Error Map Projection 119 by ray tracing through the volume to the source and applying a 3D Dose Error Kernel generated by the original assayed QA measurement versus QA calculation. The TPS Dose Data Objects 118 are aggregated or summed 121 as are the corrected patient dose field Objects 120 summed 121 by volume to create two Total Dose Objects, one being the 3D TPS Planned Object 122 and the other a Total 3D Dose Corrected Patient object 123. Dose volume histograms (DVH) are created 124 from each of the Total Dose Objects 122, 123 using the TPS structures data object (not shown) and plotted for comparison 125. The Total Dose Corrected object is also exported into the TPS where the dose review takes place in the TPS system 126.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the claims herein presented and supported by this disclosure.

That which is claimed is:

1. A method of determining a patient dose during or prior to therapy by an external radiation beam from a source of radiation, the method comprising:
   determining a dose distribution from a patient plan as delivered in a QA phantom at each of a plurality of beam angles;
   comparing the determined dose distribution at each beam angle to a corresponding treatment planning system (TPS) dose modeled distribution in the QA phantom, with the comparing resulting in a correction distribution that when applied to the TPS dose modeled distribution results in the determined dose distribution;
   geometrically projecting the correction distribution relative to the source of radiation through a volume that represents a dose volume of the TPS for a patient beam for each beam angle; and
   applying the correction distribution to the TPS patient dose volume for each beam angle for providing a corrected dose distribution in the patient for each beam angle.

2. The method of claim 1, wherein the determining comprises at least one of measuring and calculating.

3. The method of claim 2, wherein the calculating comprises calculations for radiation transport in radiotherapy dosimetry and treatment planning.

4. The method of claim 2, wherein the dose distribution measuring comprises measuring dose with at least one of a film, a diode array, an ion chamber array, and an electronic portal imaging device (EPID).

5. The method of claim 2, wherein the dose distribution measuring comprises measuring dose with a three dimensional detector array.

6. The method of claim 2, further comprising employing the processor for interpolating the correction distribution from the measured dose to non-measured points for each beam angle, wherein the geometrically projecting comprises geometrically projecting the interpolated correction distribution, and wherein the correction distribution applying to the TPS patient dose volume comprises applying the interpolated correction distribution.

7. The method of claim 1, further comprising employing the processor for generating a dose error kernel for sub-beamlets of the beam based on the determined dose distribution;, and wherein the geometrically projecting comprises the processor geometrically applying the dose error kernel divergently from the source.

8. The method of claim 1, further comprising comparing the processor applying the corrected dose distribution to the TPS dose modeled distribution.

9. The method of claim 1, further comprising aggregating all beam angle corrected dose distributions into the total patient dose distribution being executed by the processor.

10. The method of claim 9, further comprising comparing the corrected total dose distribution to the TPS total dose distribution being executed by the processor.

11. The method of claim 9, further comprising reducing the corrected total dose distribution by patient structure analysis to dose volume histograms and the processor comparing the dose volume histograms to TPS total dose volume histograms.

12. The method of claim 1, further comprising reducing the corrected dose distribution by patient structure analysis to dose volume histograms and comparing the dose volume histograms to TPS dose volume histograms being executed by the processor.

13. The method of claim 1, further comprising exporting the corrected dose distribution held in memory of the processor to the TPS for reviewing thereof.

14. The method of claim 1, further comprising providing the phantom having various materials simulating heterogeneities in the patient.

15. A system for determining a patient dose during or prior to therapy from an external radiation beam from a source of radiation, the system comprising:
   means for determining a dose distribution from a patient plan as delivered in a QA phantom at each of a plurality of beam angles; and
   a processor for comparing the determined dose distribution at each beam angle to a corresponding treatment planning system (TPS) dose modeled distribution in the QA phantom, with the comparing by the processor resulting in a correction distribution that when applied to the TPS dose modeled distribution results in the determined dose distribution,
   wherein the processor geometrically projects the correction distribution relative to the source through a volume that represents a dose volume of the TPS for a patient beam for each beam angle, and
   wherein the processor applies the correction distribution to the TPS patient dose volume for each beam angle for providing a corrected dose distribution in the patient for each beam angle.

16. The system of claim 15, wherein the determining means comprises at least one of means for measuring and means for calculating.

17. The system of claim 16, wherein the dose distribution measuring means comprise at least one of a film, a diode array, an ion chamber array, a three dimensional detector array, and an electronic portal imaging device (EPID).

18. The system of claim 16, wherein the processor interpolates the correction distribution to non-measured points for each beam angle, and wherein the geometric projecting of the correction distribution includes the processor geometrically projecting the interpolated correction distribution, and wherein the applying of the correction distribution includes the processor applying the interpolated correction distribution.

19. The system of claim 16, wherein the calculating means comprises calculation means for radiation transport in radiotherapy dosimetry and treatment planning.

20. The system claim 15, wherein the processor is executed for generating a dose error kernel for sub-beamlets of the beam based on the determined dose distribution; and wherein the geometric projecting comprises the processor geometrically applying the dose error kernel divergently from the source.

21. The system of claim 15, wherein the processor is operated for comparing the corrected dose distribution to the TPS dose modeled distribution.

22. The system of claim 15, wherein the processor is operated for aggregating all beam angle corrected dose distributions into the total patient dose distribution.

23. The system claim 22, wherein the processor is operated for comparing the corrected total dose distribution to the TPS total dose distribution.

24. The system of claim 22, wherein the processor is operated for reducing the corrected total dose distribution by patient structure analysis to dose volume histograms and for comparing the dose volume histograms to TPS total dose volume histograms.

25. The system of claim 15, wherein the processor is operated for reducing the corrected dose distribution by patient structure analysis to dose volume histograms and comparing the dose volume histograms to TPS dose volume histograms.

26. The system of claim 15, wherein the processor is operated for exporting the corrected dose distribution to the TPS for reviewing thereof.

27. The system of claim 15, wherein the phantom comprises materials simulating heterogeneities in the patient.

28. A method of delivering a dose to a patient from an external radiation beam from a source of radiation, the method comprising:
    determining a dose distribution from a patient plan as delivered in a QA phantom at each of a plurality of beam angles;
    comparing the determined dose distribution at each beam angle to a corresponding treatment planning system (TPS) dose modeled distribution in the QA phantom, with the comparing resulting in a correction distribution that when applied to the TPS dose modeled distribution results in the determined dose distribution;
    geometrically projecting the correction distribution relative to the source of radiation through a volume that represents a dose volume of the TPS for a patient beam for each beam angle;
    applying the correction distribution to the TPS patient dose volume for each beam angle; and
    delivering a corrected dose distribution to the patient for each beam angle.

29. The method of claim 28, wherein the dose distribution determining comprises measuring dose with at least one of a film, a diode array, an ion chamber array, and an electronic portal imaging device (EPID).

30. The method of claim 28, wherein the dose distribution determining comprises measuring dose with a three dimensional detector array.

31. The method of claim 28, further comprising interpolating the correction distribution from a measured dose to non-measured points for each beam angle, wherein the geometrically projecting comprises geometrically projecting the interpolated correction distribution, and wherein the correction distribution applying to the TPS patient dose volume comprises applying the interpolated correction distribution.

32. The method of claim 28, further comprising generating a dose error kernel for sub-beamlets of the beam based on the determined dose distribution, and wherein the geometrically projecting comprises geometrically applying the dose error kernel divergently from the source.

33. The method of claim 28, further comprising comparing the corrected dose distribution to the TPS dose modeled distribution.

34. The method of claim 28, further comprising aggregating all beam angle corrected dose distributions into the total patient dose distribution.

35. The method of claim 34, further comprising comparing the corrected total dose distribution to the TPS total dose distribution.

36. The method of claim 34, further comprising reducing the corrected total dose distribution by patient structure analysis to dose volume histograms and comparing the dose volume histograms to TPS total dose volume histograms.

37. The method of claim 28, further comprising reducing the corrected dose distribution by patient structure analysis to dose volume histograms and comparing the dose volume histograms to TPS dose volume histograms.

38. The method of claim 28, further comprising exporting the corrected dose distribution to the TPS for reviewing thereof.

39. The method of claim 28, further comprising providing the phantom having various materials simulating heterogeneities in the patient.

* * * * *